United States Patent [19]

Warriner

[11] Patent Number: Plant 6,653

[45] Date of Patent: Mar. 7, 1989

[54] ROSE PLANT JACHOP

[75] Inventor: William A. Warriner, Tustin, Calif.

[73] Assignee: Jackson & Perkins Company, Medford, Oreg.

[21] Appl. No.: 75,055

[22] Filed: Jul. 17, 1987

[51] Int. Cl.[4] ..... A01H 5/00

[52] U.S. Cl. ..... Plt./18

[58] Field of Search ..... Plt./18

*Primary Examiner*—Robert E. Bagwill

*Attorney, Agent, or Firm*—Majestic, Gallagher, Parsons & Siebert

[57] ABSTRACT

A rose variety of the hybrid tea class is providing having extremely long cutting stems averaging about 22 inches to 30 inches in length, a very fast cut flower cycle of large pink flowers, and is suitable for greenhouse cut flower production.

1 Drawing Sheet

SUMMARY OF THE INVENTION

The present invention relates to a new and distinct variety of rose plant of the hybrid tea class, which was originated by me by crossing the variety Bridal Pink, U.S. Plant Pat. No. 2,851, with the variety Grand Masterpiece, U.S. Plant Pat. No. 4,767.

The primary objective of this breeding was to produce a new rose variety of the hybrid tea class that had large pink flowers and was suitable for greenhouse cut flower production. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. High cut flower production;
2. Unusually long stems;
3. Fast cycle time for cut flowers;
4. Resistance to powdery mildew;
5. Occurrence of seven leaflet leaves;
6. Presence of heavily appendaged stipules.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jachop". Color terminology is in accordance with The Royal Horticultural society Colour Chart except where an ordinary dictionary significance for the color is apparent.

Observations of the buds and flowers were made from specimens grown in a greenhouse at Irvine, Calif. from December to June.

Flower

The blooming habit is continuous. The bud size is one and three-fourths inches when the petals start to unfurl. The bud form is long, pointed ovoid. The bud color when sepals first divide is near Red Group 52A; when half blown, the upper side of petals is near Red Group 52A to 52B and the lower side of petals is near Red Group 52A to 52B. The sepals have a color near Green Group 138B. The surface texture is covered with fine hairs. There are three appendaged sepals normally to heavily appendaged, and two unappendaged sepals with hairy edge. The receptacle color is near Green Group 143C with a funnel shape, small to medium size and a few fine hairs on the surface. The peduncle is medium to short length, and glandular surface. Peduncle color is medium green and the peduncle is stiff and erect.

Bloom

Bloom size is large, with an average open size of four and one-half inches, borne singly. The stems are very long. The form when first open is high center. This form then flattens and the outer petals curl back, quill fashion. Under normal conditions there are 25 to 30 petals. The upper side of petals is near Red Group 52A to 52B, as is the reverse side of the petals. The base of petals has a small yellowish-white half moon at the point of attachment to the peduncle with the major color being near Red Group 52A. There are no variegations. The general tonality at the end of the first day shows no change in color. At the end of the third day, there is a slight fading to near Red Group 52C.

The fragrance is slight. The petal texture is thin, of a deltoid shape and with a pointed tip, with the tips being slightly recurved and the edges slightly quilled.

The arrangement is imbricated with few, medium petaloids in the center. The blooms drop off cleanly, and last on the plant for a long period and as a cut flower for a long time.

Reproductive Parts

The anthers are large and many, of yellow to reddish brown color and arranged regularly around the styles and mixed with the petaloids. The filaments are reddish brown, the pollen is gold yellow, the styles are reddish, and the stigmas are greenish yellow.

Plant

A very vigorous growth of upright bush form.

Foliage

Medium size, normal in quantity. The new foliage is light green with reddish margin, and the old foliage is dark green and dull. Normal mid-stem leaves have five to seven leaflets.

The leaflets are of an oval pointed shape, are smooth, and have a serrated edge. The serration is single and small in size. Petiole rachis is green with a reddish cast, and a smooth underside. Stipules are medium. The foliage is resistant to mildew under normal growing conditions at Irvine, Calif.

Wood

New wood is light green, with a smooth bark. Old wood is green with a smooth bark.

Prickles

There are few prickles on main canes from the base and on laterals from the main canes. The form is medium, straight and downward. Color when young is red.

Small Prickles

There are no small prickles on the main stalks or on the laterals.

Additional Distinguishing Traits

This novel rose plant has extremely long cutting stems averaging 22 inches to 30 inches in length with over about 30% beyond 26 inches. This rose plant also has a very fast cut flower cycle period — less than about 45 days in the Winter and about 40 days in the Summer at Irvine, Calif.

Parentage

The seed parent was Bridal Pink, U.S. Plant Pat. No. 2,851. The pollen parent was Grand Masterpiece, U.S. Plant Pat. No. 4,767.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by rapid, high production of cut flowers with very long stems, resistance to powdery mildew, heavily appendaged stipules and seven leaflet leaves.

* * * * *

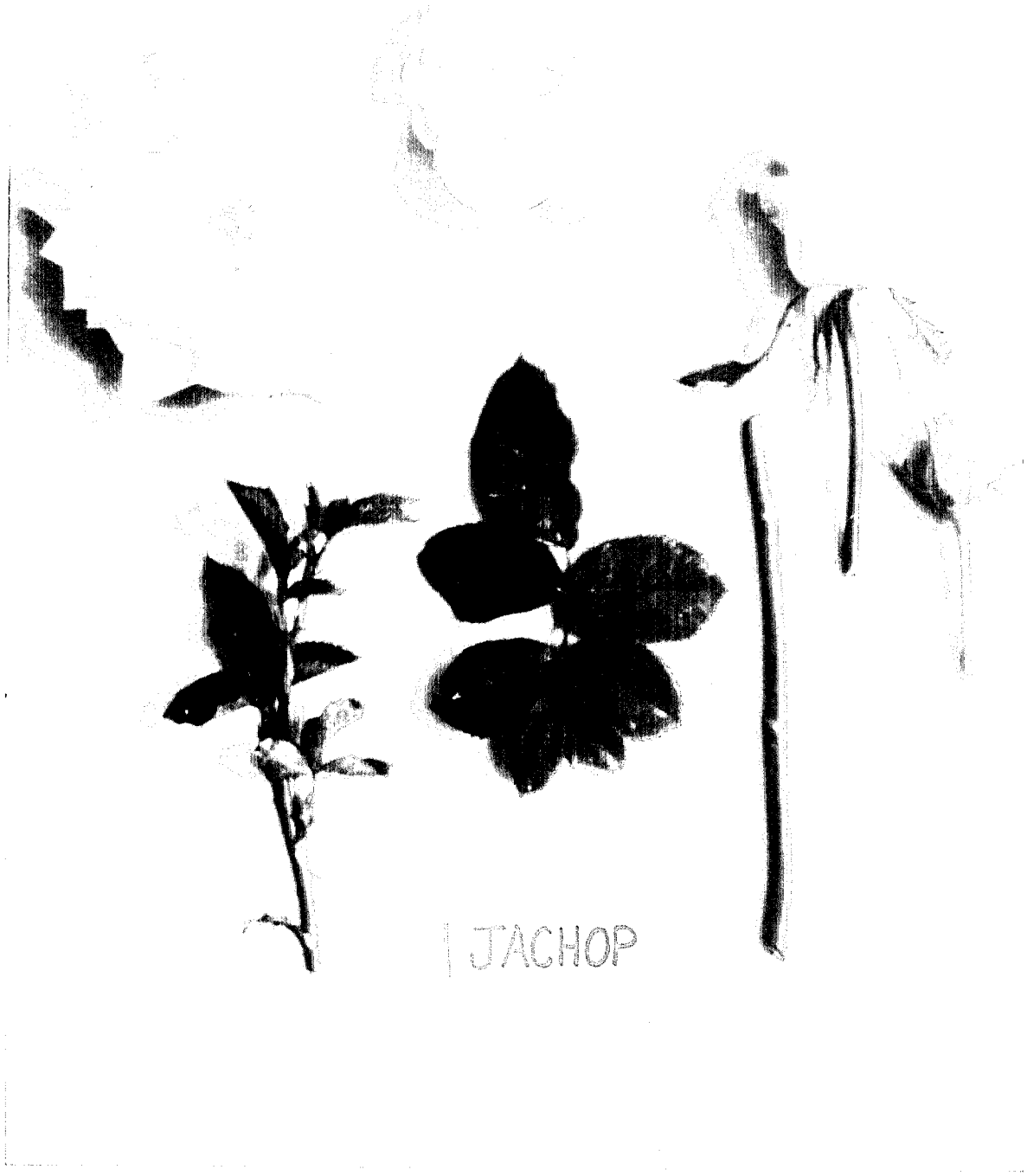
JACHOP